United States Patent [19]

Burnouf-Radosevich et al.

[11] Patent Number: 5,408,039
[45] Date of Patent: Apr. 18, 1995

[54] PROCESS FOR AN INDUSTRIAL-SCALE PREPARATION OF A STANDARDIZED HUMAN VON WILLEBRAND FACTOR CONCENTRATE OF VERY HIGH PURITY AND SUITABLE FOR THERAPEUTIC USE

[75] Inventors: Miryana Burnouf-Radosevich; Thierry Burnouf, both of Wavrin, France

[73] Assignee: Centre Regional de Transfusion Sanguine de Lille, Lille, France

[21] Appl. No.: 846,852

[22] Filed: Mar. 6, 1992

[30] Foreign Application Priority Data

Mar. 8, 1991 [FR] France ................ 91 02804

[51] Int. Cl.$^6$ .................. C07K 15/06; C07K 3/18; C07K 3/28
[52] U.S. Cl. .................. 530/383; 530/363; 530/381; 530/413; 530/416
[58] Field of Search .............. 530/381, 383, 416, 413, 530/363

[56] References Cited

U.S. PATENT DOCUMENTS

| | | | |
|---|---|---|---|
| 4,728,594 | 7/1981 | Amrani | 530/381 |
| 4,970,300 | 11/1990 | Fulton et al. | 530/363 |
| 5,006,642 | 4/1991 | Newman et al. | 530/413 |

OTHER PUBLICATIONS

Vox Sanguinis, vol. 60, No. 1, (1991) pp. 8-15, T. Burnouf et al: 'A highly purified factor VIII;c Concentrate prepared from cryoprecipitate by . . . .
Chemical Abstracts, vol. 96, No. 19, (1982), Abstract No. 158527, p. 379.
Search Report.

*Primary Examiner*—Howard E. Schain
*Assistant Examiner*—P. Lynn Touzeau
*Attorney, Agent, or Firm*—Birch, Stewart Kolasch & Birch

[57] ABSTRACT

The invention relates to a process for purifying human von Willebrand factor from a cryoprecipitated plasma fraction, which comprises a combination of three chromatographic separation steps. The first chromatographic separation step comprises contacting a cryoprecipitated fraction with a large-pore vinyl polymer resin having DEAE group. The effluent from this separation step is again contacted with a large pore vinyl polymer resin having DEAE groups in the second chromatographic step. In the third chromatographic separation step, the effluent from the second step is subjected to affinity chromatography by contacting with gelatin-Sepharose. The concentrate obtained has very high specific activity and a high percentage of high molecular weight multimers. The concentrate is intended, in particular, for therapeutic use.

7 Claims, 2 Drawing Sheets

PROCESS FOR AN INDUSTRIAL-SCALE PREPARATION OF A STANDARDIZED HUMAN VON WILLEBRAND FACTOR CONCENTRATE OF VERY HIGH PURITY AND SUITABLE FOR THERAPEUTIC USE

FIELD OF INVENTION

The invention relates to a process for preparing an industrial-scale, standardized human von Willebrand factor concentrate of very high purity, very high specific activity, and high content of high molecular weight multimers, intended in particular for therapeutic use.

BACKGROUND OF RELATED ART

Von Willebrand factor (vWF) is the largest known molecule circulating in plasma. It exists as a series of large disulfide-linked multimers, the basic subunit of which has a molecular weight of about 260 kilodaltons (KDa). The smallest form of vWF in plasma is a dimer of about 440–500 KDa and the largest forms are multimers of the dimer with molecular weights reaching up to 20 million daltons. The assembly of subunits which are linked together may be cell specific, the vWF being synthesized and polymerized in the megacaryocytes and endothelial cells.

This factor plays an essential role in hemostasis through two distinct functions: it transports and stabilizes factor VIII in the blood stream and, as an adhesive protein, it permits the spreading, the attachment and the aggregation of the blood platelets on the vascular subendothelium thus contributing to the swift healing of injured vessels.

A congenital vWF deficiency, or a structural anomaly of this factor, gives rise to von Willebrand disease which initially takes the form of hemorrhages, particularly cutaneous and of the mucous membranes. The clinical forms taken by this disease are very heterogenous and pose major problems in the event of surgery. Treatment of von Willebrand disease is essential in order to correct primary hemostasis (bleeding time) and coagulation (activated cephalin time and F VIII activity) anomalies.

The disease is treated by substitute therapy with vWF-enriched human plasma derivatives (for example, the cryoprecipitated fraction of plasma or the concentrates of Factor VIII containing a sufficient quantity of vWF). However, these products are not standardized for the treatment of von Willebrand disease. In addition, the poorly purified fractions of blood plasma, especially cryoprecipitate, are not free from the risk of viral contamination because they are often not subjected to any efficient viral inactivation step. Furthermore, they lead to an excess of contaminating proteins which the patient does not need and which can cause immune reactions after multiple injections.

Purified Factor VIII, on the contrary, can be subjected to efficient virus inactivation treatment, but its purification process has been optimized for treating hemophilia A patients and not for vWF deficient-patients. In fact, the recently developed and increasingly effective processes, such as immunoaffinity or ion exchange purification used for preparing Factor VIII, produce concentrates that no longer contain enough vWF to be efficient in the treatment of von Willebrand disease.

It is to meet this need of an efficient way for treating von Willebrand disease that the Applicants have developed a new industrial process for purifying vWF while still obtaining optimum benefit from the isolation of different plasma molecules. In particular, it permits, in one step, the preparation of a concentrate of Factor VIII (according to a process described in EP Application 0 359 593) and to recover a separate vWF fraction from the same batch of cryoprecipitate, thus allowing the optimal use of human plasma. The vWF fraction thus obtained is purified by two additional chromatographic steps which provide a vWF concentrate of very high purity.

The complexity of the vWF molecule makes it very difficult to purify. Small-scale methods, i.e., 5 to 2000 ml for the purposes of analytical study, have already been described (Thorell et al., Thromb. Res. 1984, 35: 431–450), but it has not been possible to adapt these methods for vWF preparation on an industrial scale. In addition, the concept of making the best possible use of cryoprecipitate by producing vWF in addition to FVIII was not considered.

vWF has been purified by differential solubilization on sulfated compounds in the presence of glycine (Berntorp et al., Vox Sang. 1989, 56: 212), sulfated compounds (Winkelman et al., Vox Sang. 1989, 57: 97) and by using different methods of chromatographic separation, such as molecular size exclusion (Perret et al., Haemostasis 1984, 14: 289) and ion exchange (Austen et al., Thromb Haemostas. 1982, 48: 295). However, these techniques give either low yields of vWF or have a low gel capacity, or do not make the simultaneous isolation of FVIII and vWF possible, which make them less convenient for an industrial application.

In addition, Berntorp et al. (Vox Sang. 1989, 56: 212) obtain a vWF of low purity: 45 U Ag/mg protein (p. 213) whereas the Applicants obtain 205 U Ag/mg protein. Similarly, Winkelman et al. (Vox Sang. 1989, 57: 97) obtain 10 U Ag/ml protein (p. 101).

Perret et al. (Haemostasis 1984, 14: 289), perform a defibrination step (to eliminate fibrinogen as fibrin molecules) with the use of calcium as well as enzymes from snake venom. This renders the preparation obviously unsuitable for therapeutic purposes. Moreover, gel filtration systems such as the one used by Perret et al. are hardly compatible with industrial scaling up, since they allow a flow rate of only 10 cm/h or less and show a high risk of plugging, especially in the presence of fibrinogen and fibronectin. Also the purification factor is known to be usually low due to the poor resolution of proteins in this chromatographic system.

Austen et al. (Throm. Hacmostas. 1982, 48: 46) also obtain a low purity concentrate (8 U Ag/mg protein) and relatively low yield, probably due to their drastic chromatographic conditions (pH 5.5).

Harrisson et al. (Thromb. Res. 1988, 50: 295) use dextran sulfate-sepharose as a chromatographic matrix; this material has a low retention capacity for the vWF. As a result, they obtain a vWF preparation of low specific activity: 2–4 U/mg protein (p. 301).

Finally, most of these products contain a rather large proportion of denatured or inactive forms of vWF as evidenced by the ristocetin cofactor activity (RCo)/antigen ratio ranging from 0.08 to 0.8 (Lawrie et al., Br. J. Haematol. 1989, 73: 100). This makes these products less efficient for therapeutic use in von Willebrand disease. On the contrary, the Applicant's procedure allows the recovery of vWF with a RCo/antigen ratio higher than unity, which is comparable to that of native vWF from normal pool plasma.

SUMMARY OF THE INVENTION

The present invention relates to an industrial process for preparing a vWF concentrate for therapeutic use as a by-product of a high-purity FVIII production process, enabling standardized batches, characterized by a high content in high molecular weight multimers, to be produced from very large volumes of plasma (4000 liters or more), and allowing optimal use of cryoprecipitate.

More particularly, the present invention relates to a process for preparing a vWF concentrate that comprises the combination of three successive chromatographic steps allowing an enrichment in high molecular weight multimers which are related to the vWF biological activity. The starting material is the cryoprecipitated fraction of human plasma subjected to a conventional prepurification step involving adsorption on aluminum hydroxide. This material then undergoes vital inactivation, for example using a solvent-detergent treatment, before it is purified.

DETAILED DESCRIPTION OF THE PREFERRED EMBODIMENTS

Figure 1:
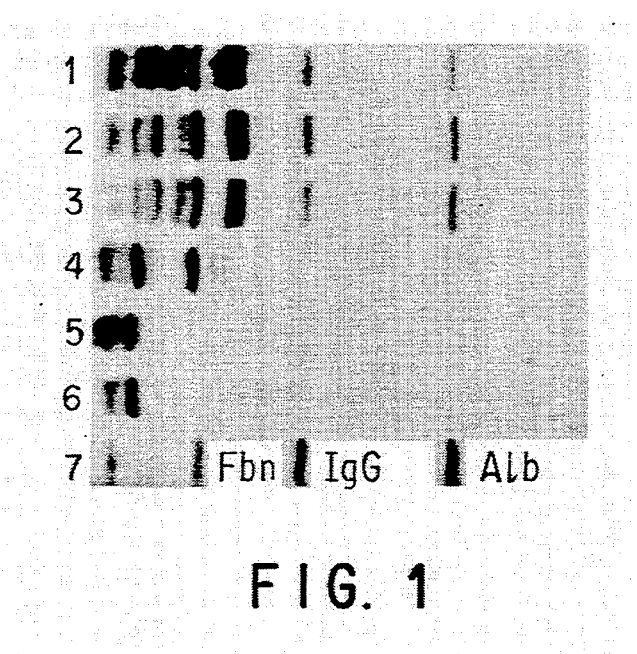
FIG. 1. SDS-PAGE of vWF purification fractions. Lane 1: cryoprecipitate; lane 2: SD-treated cryoprecipitate; lane 3: unbound DEAE-FRACTOGEL fraction; lane 4: 1st vWF eluate; lane 5: 2nd vWF eluate; lane 6: unbound gelatin fraction; lane 7: standards. Fbn=fibronectin; IgG=Immunoglobulin; Alb=albumin.

The purification process according to the present invention comprises a combination of three successive chromatographic steps from a by-product fraction of a FVIII production process, the first two involving ion exchange chromatography, and the third, affinity chromatography.

The two ion exchange chromatography steps are carried out on the same vinyl polymer resin onto which are fixed diethylamino ethyl (DEAE) groups, more particularly on columns of DEAE-Fractogel® TSK 650 (Merck), equilibrated with a buffer solution containing 0.01M trisodium citrate, 0.11M sodium chloride, 0.001M calcium chloride, 0.12M glycine and 0.016M lysine, pH 7.

DEAE-Fractogel TSK® 650 is a synthetic hydrophilic gel medium. The support is a copolymer of oligoethyleneglycol, glycidinemethacrylate and pentaerythritol-dimethacrylate to which diethylaminoethyl groups, i.e., —O—$CH_2$—$CH_2N^+(C_2H_5)_2HCl$, are attached, resulting in a weakly alkaline anion exchanger. DEAE-Fractogel® TSK 650 is available in two particle size ranges (when moistened with water): Type S (0.025–0.050 mm) and Type M (0.045–0.090 mm). Both types are useful in carrying out the present invention.

The cryoprecipitated plasma fraction, which has been prepurified and has undergone vital inactivation treatment according to conventional procedures, is applied to the first chromatographic column which retains a large proportion of the vWF. vWF is then eluted by increasing the sodium chloride concentration of the buffer solution to 0.14–0.15M.

The fraction thus eluted, enriched in vWF, is applied to the second chromatographic column under the same conditions as the first. Since many of the proteins (especially FVIII and fibronectin) which competed for the adsorption sites have already been eliminated from this fraction during the first chromatographic step, the capacity for adsorbing the vWF on the second column is advantageously far greater. After the filtrate has been removed and the column has been rinsed with the equilibration buffer solution, the adsorbed vWF is eluted by increasing the sodium chloride concentration of the buffer solution to 0.15–0.17M. Due to the excellent capacity and efficiency of the DEAE Fractogel ® resin for vWF, vWF can be eluted from the column at a very high potency (>150 U RCo/ml). Thus, the mechanical stress of ultrafiltation that would be needed to concentrate the product can be avoided.

The fraction thus eluted is subjected to affinity chromatography on a gelatin-derived gel in the same equilibration buffer solution thus avoiding any dialysis or ultrafiltration step to modify the salt composition; this column is essential to retain the molecules of residual fibronectin that still contaminate the vWF. The choice of gelatin-derived gel is not critical, however: Gelatin-Sepharose, Gelatin-Ultrogel®, Gelatin-Spherodex® and Gelatin-Fractogel® are all suitable for this purpose. Gelatin-Sepharose may be the best choice since it fixes 5 to 10 mg fibronectin/ml gel under the conditions used for the present process.

Under the conditions used the highly purified vWF does not bind on the gel and is thus eluted in the filtrate; as the gelatin affinity step does not induce extensive dilution of the vWF fraction, the product can be directly dispensed without any need for a concentration step by, e.g., ultrafiltration. The absence of proteolytic enzymes in the final product makes it very stable during the sterile filtration and freeze-drying steps, without any need for stabilizing agents.

The von Willebrand factor concentrate obtained using the process according to the present invention has an exceptionally high purification factor of >10,000 fold in relation to the initial plasma, and its specific activity is 345 U CBA/mg protein (units of measurement for the collagen binding activity), and >100 U RCo/mg protein (units of ristocetin cofactor activity).- The contribution of each chromatographic step to purifying vWF is illustrated in FIG. 1.

Figure 2:
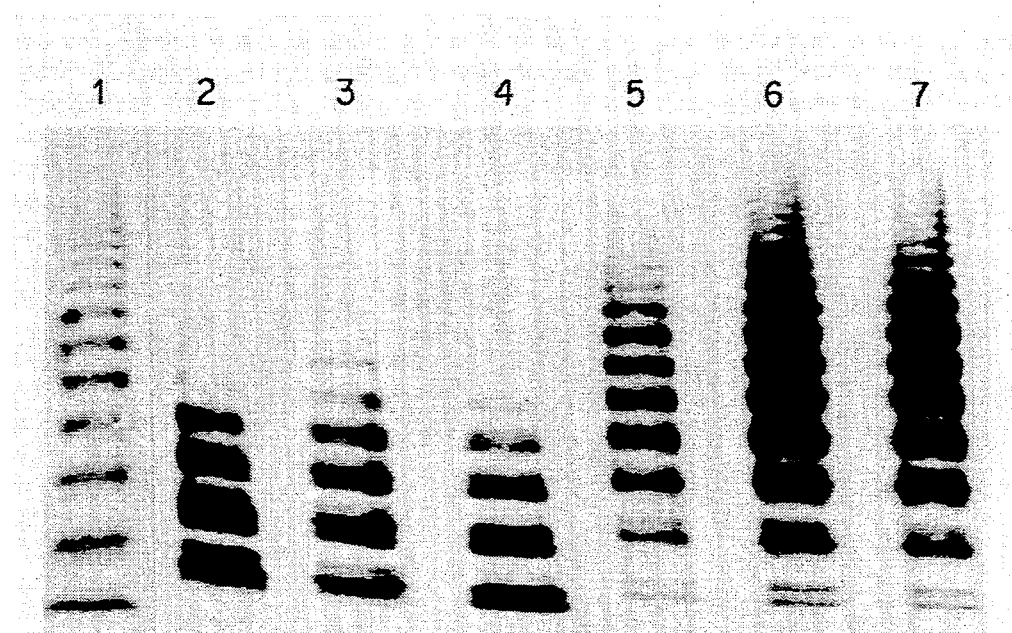
FIG. 2. Multimer distribution of vWF purification fractions. Lane 1: normal plasma; lane 2: cryoprecipitate; lane 3: SD-treated cryoprecipitate; lane 4: unbound DEAE-FRACTOGEL fraction; lane 5: 1st vWF eluate; lane 6: 2nd vWF eluate; lane 7: unbound gelatin fraction.

Quite importantly, improvement in the quality of the product during the successive purification steps was monitored as a function of the proportion of high molecular weight multimers (the molecular forms of vWF having high biological activity) as detected by electrophoretic analysis. Interestingly, this analysis reveals a progressive enrichment in multimers $\geq 4$ (FIG. 2), which represent 79% of the vWF polymers even though cryoprecipitation eliminates half of them. Unexpectedly, it is the chromatography on DEAE-Fractogel® TSK 650 that favors this selective retention of the very large multimers and eliminates with the filtrate those forms having small size, abnormal structure (having undergone partial proteolysis) and low activity.

The standardized vWF concentrate of high purity, high specific activity and high content in high molecular weight multimers, obtained by the process according to the present invention is thus particularly well suited to therapeutic use in the different forms of von Willebrand disease, as confirmed by preliminary clinical studies.

Preliminary clinical tests have shown that this concentrate led to an efficient shortening of the bleeding time during hemorrhages.

In vitro tests have confirmed that its biochemical and physiological properties are identical to those of the native molecule, in particular its ability to fix blood platelets in a perfusion device, and its ability to bind in-vivo endogenous Factor VIII.

Due to its high purity, the vWF obtained during the process according to the present invention could also be considered for various laboratory applications (fine structural analysis, functionality studies, diagnoses, etc.) and for the production of specific antibodies.

The concentrate according to the present invention can also be used as a stabilizer during the production of Factor VIII by cells transformed by genetic engineering, as well as during the purification of the Factor VIII thus produced.

The following example illustrates one form of an embodiment of the present invention without, however, limiting the scope thereof.

EXAMPLE

Starting Material

The cryoprecipitate is prepared from fresh plasma collected in the presence of sodium citrate (4%) or CPD (citrate, phosphate, dextrose) anticoagulant solution and frozen at the most 6 hours after being obtained. The plasma is deep frozen to −60° C., then preserved at −35° C. The plasma batches contain 1800 to 2000 liters which are pooled into 4000-liters batches for each application of the process. For the purpose of thawing, the plasma is placed in a temperature-regulated chamber for 12 hours to ensure slow, regular warming to −7° C., then thawed in a thermostatically controlled enclosure at 0° to 2° C. with constant stirring. The cryoprecipitate (which represents about 9 g/l plasma) is recovered by cold centrifugation.

After centrifuging, the cryoprecipitate recovered is resolubilized and adsorbed on aluminum hydroxide to remove some contaminants, i.e. the components of the prothrombin complex (particularly Factor VII) and Factor XII. The supernatant is then cooled to 15° C. (which partially removes the fibrinogen and the fibronectin).

This treatment permits the recovery of 80 to 86% of the Factor VIII/vWF mixture from the cryoprecipitate; the specific activity of the Factor VIII represents 0.7 IU/mg, and that of the vWF 0.6 U RCo/mg (ristocetin cofactor activity) and 1.2 U CBA/mg (collagen binding activity).

Viral Inactivation Treatment

The solution containing the Factor VIII/vWF mixture is subjected to a solvent-detergent treatment known for its efficiency in destroying lipid enveloped viruses (Horowitz et al., Transfusion, 1985, 25: 516) and which includes incubation for 8 hours at 25° C. in the presence of 0.3% of tri-n-butyl phosphate (TnBP) and 1% of Tween 80.

After this treatment, 95% of the activity of Factor VIII and vWF measured in the preceding step is recovered. Electrophoresis can be used to confirm that the vWF is still in multimeric form.

Chromatographic Separation Process

The purification of the vWF is derived from the Factor VIII purification process disclosed by the Applicant in European patent application No. EP 0,359,593.

The first chromatography is carried out on a column of DEAE-Fractogel® TSK 650 (Type S or M) (Merck). The equilibration buffer solution contains trisodium citrate (0.01M), calcium chloride (0.001M), glycine (0.12M), L-Lysine (0.016M) and 0.11M sodium chloride. The vWF, Factor VIII and fibronectin are retained by the column; the contaminating proteins (chiefly fibrinogen and some IgG) loosely fixed or not fixed by the column and the virus sterilizing agents are eliminated by several successive washings with the same buffer solution.

The column is used at a linear flow rate of 100 cm/h. Under these working conditions, the column used has a vWF retention capacity of approximately 75% of the amount injected (measured as the antigen, Ag) the remainder being lost in the filtrate. This binding capacity corresponds to 45 U of vWF Ag/ml gel.

The vWF is desorbed from the column by increasing the NaCl concentration of the buffer solution to 0.15M. The fraction of vWF harvested contains 30 to 35% of the initial vWF while 40% of it remains co-adsorbed with the Factor VIII which will be co-eluted by a second increase in the NaCl concentration of the buffer solution to 0.25M and then co-purified.

The fraction containing the vWF eluted from this first column is reinjected onto a second identical column, after a slight dilution with the equilibration buffer, in order to adjust the ionic strength of the vWF fraction down to an equivalent of 0.11M sodium chloride.

Since the contaminants and the Factor VIII which competed with the vWF for the adsorption sites of tile first column were almost eliminated during the first chromatographic step, binding capacity of the second column is much greater: 320 U of vWF Ag/ml gel.

The vWF is desorbed by increasing the NaCl concentration of the buffer solution to 0.17M.

This second chromatography permits a concentration rate 8 to 10 times that of the previous one, which eliminates the need for any additional concentration steps by ultrafiltration, for example. Using standardized techniques, the eluate is found to contain the following vWF quantities or activities:

| | |
|---|---|
| Antigen (Ag) | 88 ± 9 IU/ml |
| Ristocetin cofactor (RCo) | 97 ± 19 IU/ml |
| Collagen binding activity (CBA) | 149 ± 13 IU/ml |
| High molecular weight multimers (≧4 multimers) | 79% |

The CBA units (collagen binding activity) are quantified by ELISA as described by Brown and Bosak, (Thromb. Res. 1986, 43: 303). A standard plasma, calibrated against the 2nd British Standard (86/717), was used as a reference to express the values in terms of international units.

The CBA/Ag ratio of 1.69 shows that the activity of the vWF is well preserved. This is in agreement with the high percentage of high molecular weight multimers (79%) and compares favorably with that of native vWF (70%) from plasma.

Electrophoretic analysis of this vWF eluate reveals a slight contamination by fibronectin and inter-alpha trypsin inhibitor, a serine-protease inhibitor.

The second vWF eluate is then subjected to a third step of purification on a column of gelatin-Sepharose CL4B (Pharmacia) equilibrated with the elution buffer solution of the preceding column, in order to eliminate fibronectin.

This affinity chromatographic gel has a fibronectin retention capacity of >5 mg/ml, which enables this contaminant to be reduced to undetectable quantities (<4 mg/l) in the vWF fraction.

The purified vWF of the present invention is found in the filtrate of this last step and can be directly dispensed and freeze-dried.

Electrophoretic analysis of the final product can no longer detect any contaminants. The vWF content is 205 U Ag/ml protein and its specific activity is 345 U CBA/mg protein and 186–220 U RCO/mg protein.

The total degree of purification in relation to the initial plasma is >10,000 fold.

Electrophoretic analysis (SDS-agarose and scanning of the bands) demonstrates that the vWF obtained from this purification procedure is composed of 65 to 80% of high molecular weight multimers, i.e. a proportion comparable with that of the initial plasma, which was 70%.

The stability of the concentrate was studied in a liquid state at room temperature for 24 hours: no sign of proteolytic activity or any change in specific activity could be detected.

Absence of thrombogenic activity in the concentrate was verified using the conventional tests like the non-activated partial thromboplastin time (NAPTT). Thrombin, PKA and Kallikrein were undetectable.

Therefore, no stabilizing agent needs to be added to the final vWF concentrate.

The possibility of designing a purification process specifically intended for the recovery of vWF as a by-product of a FVIII production process thus makes possible, for the first time, the production of a high-purity, highly effective therapeutic concentrate standardized for the treatment of von Willebrand disease.

The applicant claims:

1. A process for preparing a purified concentrate of human von Willebrand factor enriched in high molecular weight multimers comprising:
   (a) subjecting a cryoprecipitated fraction of plasma to a first ion exchange chromatography step comprising contacting said cryoprecipitated fraction with a large-pore vinyl polymer resin having DEAE groups attached thereto, and obtaining a first von Willebrand factor-containing effluent;
   (b) subjecting said first von Willebrand factor-containing effluent to a second ion exchange chromatography step comprising contacting said first von Willebrand factor-containing effluent with a large-pore vinyl polymer resin having DEAE groups attached thereto and obtaining a second von Willebrand factor-containing effluent; and
   (c) subjecting said second von Willebrand factor-containing effluent to an affinity chromatography step comprising contacting with gelatin-SEPHAROSE, and obtaining an effluent containing a purified concentrate of human von Willebrand factor enriched in high molecular weight multimers.

2. The process according to claim 1, wherein said cryoprecipitated fraction of plasma has been prepurified by contact with aluminum hydroxide.

3. The process according to claim 1, wherein said large-pore vinyl polymer resin having DEAE groups attached thereto in steps (a) and (b) is DEAE-Fractogel® TSK 650 equilibrated with a buffer solution containing 0.01M trisodium citrate, 0.11M sodium chloride, 0.001M calcium chloride, 0.12M glycine, and 0.016M L-lysine.

4. The process according to claim 1, wherein said first ion exchange chromatography step (a) comprises introducing said cryoprecipitated fraction of plasma to a first ion exchange chromatography column, which has been equilibrated with a buffer solution, and eluting said first von Willebrand factor containing effluent by increasing the sodium chloride concentration of said buffer solution to 0.14–0.15M.

5. The process according to claim 1, wherein said second ion exchange chromatography step (b) comprises introducing said cryoprecipitated fraction of plasma to a second ion exchange chromatography column, which has been equilibrated with a buffer solution, and eluting said second von Willebrand factor containing effluent by increasing the sodium chloride concentration of said buffer solution to 0.15–0.17M.

6. The process according to claim 1, wherein said affinity chromatography step (c) comprises selectively adsorbing residual fibronectin by introducing the effluent from said second ion exchange chromatography step (b) to a gelatin-SEPHAROSE chromatography column equilibrated with the elution buffer from said second ion exchange chromatography step (b) and obtaining an effluent containing a purified concentrate of human von Willebrand factor enriched in high molecular weight multimers.

7. The process according to claim 1, wherein said obtaining of said purified concentrate comprises collecting, dispensing, and freeze-drying the von Willebrand factor present in the effluent of said affinity chromatography step.

* * * * *